United States Patent [19]

Tsay et al.

[11] Patent Number: 4,716,120

[45] Date of Patent: Dec. 29, 1987

[54] STABLE ALLERGENIC EXTRACTS AND METHODS

[75] Inventors: Yuh-Geng Tsay, San Jose; Myron A. Beigler, Los Altos Hills; Emanuel Calenoff, Burlingame; Gerald L. Friesen, Vacaville; James L. Nichols, Los Altos, all of Calif.

[73] Assignee: Minnesota Mining and Manufacturing Company, St. Paul, Minn.

[21] Appl. No.: 801,649

[22] Filed: Nov. 25, 1985

Related U.S. Application Data

[63] Continuation of Ser. No. 476,187, Mar. 17, 1983, abandoned.

[51] Int. Cl.$^4$ .................. A61K 39/00; G01N 33/53
[52] U.S. Cl. .................. 436/513; 210/650; 424/88; 424/91; 424/98; 424/195.1; 436/531; 436/809
[58] Field of Search .............. 424/88, 91, 98, 195, 424/195.1; 210/650, 695; 422/261; 436/513, 531, 809

[56] References Cited

U.S. PATENT DOCUMENTS

| | | | |
|---|---|---|---|
| 3,983,053 | 9/1976 | Courtney et al. | 210/635 |
| 4,350,686 | 9/1982 | Relyveld et al. | 424/88 |
| 4,387,091 | 6/1983 | Vijay et al. | 424/88 |

OTHER PUBLICATIONS

Curtis, (1975), Allergenic Extracts Chapter 74, pp. 1344–1352, in: Remington's Pharmaceutical Sciences 15th Edition, Mack Publ. Co.

*Primary Examiner*—Sidney Marantz
*Attorney, Agent, or Firm*—Donald M. Sell; James A. Smith; Philip M. Goldman

[57] ABSTRACT

A storage-stable, high potency allergenic extract is prepared by ultrafiltration, retaining fractions having molecular weights of from 1000 to 100,000, and treating the solution with gel polymer and/or carbon absorbents. The extract is dried to a moisture content of less than one weight percent water. The purified solution and aqueous reconstituted solutions of the dried extract provide a transparent, colorless solution which has greatly increased stability, remaining transparent and colorless for extended periods.

23 Claims, No Drawings

STABLE ALLERGENIC EXTRACTS AND METHODS

This application is a Continuation of copending application Ser. No. 476,187 filed Mar. 17, 1983 abandoned.

FIELD OF THE INVENTION

This invention relates to allergenic materials used to diagnose and treat allergic conditions in humans. More specifically, this invention relates to improved extracts from plant and animal sources prepared by improved methods which concentrate the allergenically active components in a form suitable for use in diagnosis and treatment of allergic conditions. The extracts have greatly increased storage stability prior to and during use.

BACKGROUND OF THE INVENTION

Description of the Prior Art

A wide variety of allergenic extracts and methods for preparing, storing, and using them including standard commercial procedures are described in *Remington's Pharmaceutical Sciences*, p. 1344–1352, Mack, Easton, PA 15 ed. (1975). Allergenic extracts from a wide range of natural and plant and animal sources and manufactured goods are described. Manufacturing procedures for preparing extracts including details about grinding, defatting, extraction, clarification, dialysis, concentration, sterilization and lyophilization are presented therein.

Major efforts to concentrate and standardize allergenic components of allergen extracts have been made in the past. Procedures for solvent extraction, often combined with precipitation, are described in U.S. Pats. 2,316,311, 3,148,122, 3,281,323, 3,591,677, 3,953,588, 3,995,023, 4,027,006, and 2,347,435. Ion exchange techniques are described in U.S. Pat. 2,901,398. The principal objective of these processes is to separate the active allergenic components from inactive ingredients obtained through the particular extraction procedure employed.

A number of patents describe the preparation of modified allergenic compounds wherein the allergenic component is chemically modified such as by cross-linking with formaldehyde or other reactive chemical agents. As a preliminary procedure, the allergenic extracts may be separated from low molecular weight components which would interfere with the chemical reaction. Removal of lower molecular weight components for this purpose is described in U.S. Pats. 4,226,853 (dialysis), 4,234,569 (ultrafiltration or gel filtration), 4,256,732 (dialysis), and 4,163,778 (dialysis and column chromatography). In the above procedures, the aqueous or ethanolic extract solution is treated to remove the lower molecular weight components, and the chemical reactants are added to the aqueous solution of the product to effect a chemical modification of the allergenic protein.

Of a similar nature are the papers by E. Puttonen et al, "Studies on Allergen and Allergoid Preparations for Purified Timothy (Phleum pratense) Pollen Extracts" in *Int. Arch. Allergy Appl. Immun.* vol. 68, pp 1–12 (1982). In this paper, fractionation of a dried timothy pollen extract by gel column chromatography is presented. In the procedure, a sample of the extract is fractionated with a SEPHADEX G-75 column, and active fractions are pooled and freeze-dried. One portion of the material is then reacted with formaldehyde to prepare an allergoid product, and the properties of the original and treated fractions are compared.

The freeze-dried timothy grass pollen intermediates described in the Puttonen et al article are completely different from the extracts of this invention. In the sampling of active fractions for pooling, minor allergens are discarded, and the relative ratios of allergens present in the original extract are not preserved. The freeze-dried product cannot therefore be correlated with diagnostic or desensitizing compositions which have the original allergen extract composition profile. This publication does not describe separation of plant extracts using ultrafiltration, treatment with absorbents, or lowering the moisture content of the resultant product to less than one weight percent to increase the shelf life stability thereof.

Stability studies of timothy grass pollen extracts are disclosed by M. C. Anderson et al in "Antigenic and Allergenic Change During Storage of a Pollen Extract", *J. Allergy Clin. Immunol.* 69(1) pp 3–10 (1982) and articles cited therein. Enzyme activities of timothy pollen extracts are reported, and degradation mechanisms including thermal denaturation and enzymatic breakdown of allergenic and antigenic proteins and carbohydrates are postulated. Sugar-splitting activity was reported to be inhibited in 50 percent glycerol solutions.

SUMMARY AND OBJECTS OF THE INVENTION

The purified allergenic extract of this invention has the allergen composition of the original extract and a moisture content of less than one weight percent. Upon reconstitution it yields a transparent, colorless solution which has an increase in absorbance in the range of 400 to 700 nm of less than 0.01 O.D. after storage for as long as 18 days at 22° C. The extract is preferably free from extracted components having molecular weights outside the range of 1000 to 100,000 daltons.

The process of this invention for increasing shelf life stability of allergenic extracts comprises passing a fat-free solution of the allergenic extract through 100,000 dalton and 1000 dalton filters and retaining the fraction having a molecular weight of from 1000 to 100,000. The allergenic extract is contacted with a clarifying quantity of a carbon absorbent and a gel polymer absorbent, yielding an extract having sustained transparency, even after prolonged storage. The solution is then dried to a moisture content of less than one weight percent without denaturing the allergens. The product has improved stability, as measured by the STORAGE STABILITY TEST described hereinafter, both as a moisture-free powder and as a reconstituted aqueous solution. This process can be used to increase the stability of allergenic extracts selected from the group of plant and animal extracts including pollens, molds, smuts and animal products such as epidermals, glandular elements, insects and insect venoms, and foods, for example.

One embodiment of the product of this invention comprises insoluble supports to which the allergenic extracts of this invention are adhered, such as by absorption, adsorption or chemical bonding to yield diagnostic means with greater sensitivity and specificity.

It is an object of this invention to provide stable, sterile, virus-free allergenic products derived from extracts obtained from plant and animal sources.

It is a further object of this invention to provide a more efficient process for making and stabilizing sterile, viral-free allergenic extracts obtained from plant and animal sources.

It is a further object of this invention to provide stabilized allergenic products which have greater sensitivity and specificity when used as diagnostic reagents than extracts which have not undergone this treatment.

It is a still further object of this invention to provide diagnostic supports having, thereon, the superior, stabilized, highly specific allergenic products of this invention.

DETAILED DESCRIPTION OF THE INVENTION

Desensitizing treatments with allergenic extracts corresponding to the allergen to which a patient has an allergic reaction are often used by medical specialists to treat severe allergic conditions. Allergic reactions most generally treated derive from pollens originating from trees, grasses, weeds and garden plants; epidermals and miscellaneous inhalents such as dust, tobacco, and glandular elements; molds; smuts; insects and insect venoms; and foods including animal and vegetable proteins, seafoods, eggs, milk and the like. The generally accepted medical procedure for treating severe allergic conditions involves testing with crude extracts obtained from the suspected cause of the original allergic condition and administration of the extracts to the patient in desensitizing doses. In general, the extracts are purified to remove some nonantigenic material by general procedures including some or all of the following technologies: grinding, defatting, extracting, clarifying, dialyzing, concentrating and sterilization. These procedures are relatively simple and yield antigenic materials mixed with other components derived from either the plant or animal source or the extraction procedures. Previously proposed separations by precipitation, chromatography, ultrafiltration, and solvent extraction have not been adopted because they have not been found to improve the product.

A major limitation of the currently available full strength antigenic compositions is their lack of shelf life stability. Efforts to increase stability by chemical treatment have generally reduced the antigenicity. Reconstituted extracts usually show increased color and/or turbidity after storage at room temperature for less than 7 days, clearly showing major chemical change. They must be discarded as soon as increased color or turbidity is visually evident.

The method of this invention is a process which can be easily applied using currently available technology to yield an antigenic product having no significant reduction in antigenicity. The products contain all of the representative antigenic material present in the original extract in their original proportions. The purified products of this invention are more stable than previously known formulations, can be more easily standardized and are superior allergenic products for use in diagnosis and desensitization treatments.

This process starts with the fat-free, aqueous allergenic extract and includes the separation of the allergenic extract from non-allergenic components by ultrafiltration using 1000 and 100,000 dalton filters and treatment with absorbents. Components having a molecular weight less than 1000 daltons and greater than 100,000 daltons are discarded. The retained fraction has a molecular weight of from 1000 to 100,000 and is essentially free from components having higher and lower molecular weights. The retained fraction can be dried to a moisture content of less than one weight percent to yield an antigenic product. The ultrafiltration process of this invention produces a sterile product with all of the original allergens in the ratios present in the original complete extract. This product has substantially greater shelf life stability than dried products of previously known extracts as measured by the STORAGE STABILITY TEST described hereinafter.

The mechanisms of degradation processes are not clearly understood. Studies made with only a few allergens have been reported, and there is no established common cause of instability even between the few studied. Without being limited to any theory, we believe that a significant cause of instability is due to Maillard reactions between sugars and the proteins. Not only would this directly degrade the protein and glycoprotein allergens, but it would introduce toxic reaction products in the extracts.

The ultrafiltration with a 1000 dalton filter removes sugars, amino acids and peptides which might undergo Maillard reaction changes. The ultrafiltration with a 100,000 dalton ultrafilter and treatment with absorbents efficiently removes proteolytic and starch reducing enzymes having a molecular weight above 100,000 along with bacteria, virus and non-allergenic impurities, and without disturbing the allergen content of the extract. The level of proteolytic or carbohydrate reducing enzymes would be reduced. Accordingly, the level of proteolytic activity and carbohydrate reducing activity which would convert starches to reducing sugars would be diminished. Consequent Maillard reactions would be greatly reduced because of the low levels of sugar formed. Consequently original allergen levels would be preserved, and formation of pigments and toxic by-products would be reduced or eliminated.

In the process of this invention, the allergenic extract is contacted with a clarifying quantity of a carbon absorbent and a gel polymer absorbent yielding a transparent, colorless extract which, in its original state and after drying and reconstitution, has greatly increased stability as indicated by an increase in absorbance in the range of 400 to 700 nm of less than 0.01 O.D. after prolonged storage at ambient temperatures.

The ultrafiltration procedures applied are conventional and known in the art for separation of materials. The allergenic extracts are passed through the ultrafilters as fat-free aqueous solutions. The original extract solutions are pH sensitive and can tolerate only short storage at low temperatures if outside the pH range of 6 to 8. A pH within the range of 7 to 8 during ultrafiltration is preferred. A stabilizing pH is preferably maintained with a buffer solution. Suitable buffer solutions include standard solutions such as Phosphate Buffer Solution (PBS), Coca's Solution and the like. Salt solutions such as sodium chloride solutions can also be employed. The dissolved solids concentration is not critical, concentrations of less than 50 weight percent solids being generally operable, concentrations of less than 20 weight percent being more commercially practical. Preferred concentrations are less than 5 weight percent dissolved solids, and concentrations of less than 2 weight percent are optimum. The original extracts are sensitive to temperature, and process temperatures should be within the range of 0° to 40° C. Ultrafiltration is preferably carried out at reduced temperatures to preserve the allergens, temperatures above the freezing temperatures up to 10° C. being useful, temperatures within the range of 2° to 8° C. being preferred. A temperature of 4° C. or less is optimum.

The ultrafiltration equipment and filters employed are non-critical and can be those which are generally available commercially. Ultrafiltration procedures and equipment are described in *Remington's Pharmaceutical Sciences,* supra, pp 303–304 and 1397. Equipment such as MILLIPORE PELLICON CASSETTES (Millipore Corporation, Bedford, Mass.); AMICON stirred cells, fluid channel systems, and hollow fiber systems (Scientific Systems division, Amicon Corp., Danvers, Mass.) and NUCLEOPORE stirred cell and hollow fiber systems, Nucleopore Corp., Pleasanton, Ca. can be used. Suitable 1000 dalton and 100,000 dalton filters include MILLIPORE filters PCAC 00005, PTHK 00005, PSVP 00005 and PTHK 00001; NUCLEOPORE filters A1, C1, A100, C100, and F100 and AMICON filters YMZ and XM100A.

In the preferred ultrafiltration process, the fatfree aqueous extract is processed as a buffered solution such as a phosphate buffer solution (PBS), pH 6–8, with no azide preservative. The solution is passed through a 100,000 dalton membrane. The solution is then treated with a 1000 dalton membrane filter, the liquid passing through the membrane filter being discarded, until the extract solution volume is reduced by 50 percent. The concentrate is then diluted to its original volume with water (when processing at the lowest temperatures) or preferably a buffer solution such as PBS and ultrafiltration is repeated until the liquid volume is reduced by 50 percent. The dilution and 1000 dalton ultrafiltration steps are preferably repeated at least two more times.

Ultrafiltration procedures and equipment therefor are described in *Separation Methods in Biochemistry,* Amicon publication No. 553; *Lab 50,* a Nucleopore publication, and *Laboratory products Catalogue* by Millipore.

The allergenic extract starting materials used in the process of this invention can be the conventionally available raw, undenatured extracts of the plant and animal antigens of the type which have heretofore been used for desensitization and diagnostic procedures. A full description of extraction procedures is presented in *Remington's Pharmaceutical Sciences,* supra, and the numerous patents listed above, the portions thereof directed to preparation of allergenic extracts being hereby incorporated by reference.

The source of the allergenic extract is initially subdivided, if necessary, to increase the surface area and rupture cell membranes to facilitate extraction. Materials containing little moisture may be rapidly ground in household-type blenders. Materials containing much moisture may be disintegrated and extracted in a juice-extracting machine or less efficiently in a household type food or meat grinder. Materials such as animal hairs, feathers, kapok, silk and synthetic fibers must be cut into small fragments by cutting implements.

If the material contains fats and oils, it is defatted by extracting it with organic solvents. This is necessary to prevent emulsification during the aqueous extraction process and to obtain a clear product solution. Extraction solvents useful are those in which the fat is selectively soluble but in which the watersoluble components are generally insoluble. Suitable solvents include ether, toluene, xylene and the like. In defatting, the material defatted is intimately mixed with successive portions of the organic solvent, and the organic phase is separated from the other materials. All pollens must be defatted. The extraction of materials to remove irritants (oils, resins and waxes) may require the use of multiple solvents.

In the extraction procedure, the active allergenic substances are removed from the solid materials in a aqueous phase. The active allergen fractions, because they are soluble in alkaline solutions, are generally extracted with a buffered saline solution having a pH of about 8. For example, the extraction can be carried out by macerating the material to be extracted in the extracting solvent for 12 to 72 hours with shaking or other vibration. Extraction temperatures as high as 10° C. can be used, but preferred extraction temperatures are less than 4° C. The advantage of using a buffered extracting fluid is that it neutralizes both acids and alkalinity, resisting a pH change from 8 which is the optimum pH for extraction. It also neutralizes acids and alkalinity which might prove irritating in the final product.

After the material has been extracted, the solvent containing the active ingredients is separated from the inactive material by filtration or similar procedures. The extract can then be directly processed by the ultrafiltration procedures of this invention.

Suitable raw allergenic extracts for essentially all of the most common allergens are commercially available in adequate quality to be used as the starting material in the process of this invention. For example, such allergenic extracts are products available from Hollister-Stier, a division of Cutter Laboratories, Inc.

In the preferred process of this invention, the source material can be allergenic extracts or the natural sources (pollen, danders or the like) of the extracts disclosed in the Examples.

The absorbent treatment can be carried out at any stage of the process, before ultrafiltration, after being passed through a 100,000 dalton filter or after 1000 dalton ultrafiltration. Preferably, the absorbent treatment is carried out after the ultrafiltration steps are completed because less absorbent is then required.

In the absorbent treatment, the allergen extract solution is intimately contacted with absorbent. For example, the solution can be contacted with one absorbent, then contacted with another absorbent, or it can be contacted with more than one type of absorbent in a single step. The contact can be achieved by passing the solution through a column, or by intimately mixing the solution in a stirred container and separating the solution from the absorbents by filtration.

The absorbent treatment is preferably carried out with at least sufficient absorbent to effect stabilization, that is, the minimum amount which yields a solution with increased stability. It has been found that amounts sufficient to yield a colorless, transparent solution are sufficient to achieve the increased stability. For example, treatment of extract with one volume of a swelled gel polymer such as dextran absorbent per 400 volumes of extract solution and with 70 grams of charcoal per liter of extract solution usually is sufficient.

The absorbent treatment is preferably carried out in a buffered solution at the lower temperatures described above with respect to the ultrafiltration steps, at temperatures preferably between 2° to 8° C. and a pH within the range of 7 to 8. Contact times with the absorbents is not critical if the absorbent is finely divided, contact times of 3 minutes being sufficient with finely divided particles of carbon and polymer gel absorbents.

Suitable gel polymer absorbents are polymers which form cage structures in aqueous media. Polysaccharide absorbents such as dextrans, agarose and derivatives thereof are preferred. Synthetic gel polymers such as polyacrylamides, polyvinylpyrrolidones and the like can also be used. The preferred polysaccharide absorbents are dextran and dextran derivatives such as SEPHADEX (Pharmacia). The gel absorbent can have any particle size down to 300 mesh, particle sizes in the range of from 50 to 150 mesh being preferred.

Suitable carbon absorbents include activated carbon, activated charcoal, larger charcoal particles, graphite and the like, preferably finely divided and with a particle size of less than 200 mesh. The preferred carbon absorbent is activated charcoal having a particle size of 250 to 350 mesh.

The product solution is dried to a moisture content of less than one percent. The drying must be carried out without temperature elevation to preserve the allergens. Conventional vacuum drying or freeze-drying procedures are suitable, and the procedures and equipment generally used for freeze-drying can be used. Preferably the extract solution in vials is frozen to a temperature of $-30°$ C. or below for 2 hours, and a vacuum of 20 torr or less is applied. The shelves on which the vials are supported is gradually warmed to 25° C. When the material has less than one percent moisture and reaches equilibrium (no significant weight loss after 2 hours), freeze drying is complete. Suitable equipment is described for example, in *Remington's Pharmaceutical Sciences*, supra, pp 1483–1485, the contents of which are hereby incorporated by reference.

For a product to be used in desensitization procedures, the liquid product of the ultrafiltration is preferably fed directly into sealable vials, and the product can be freeze-dried in the vials in which they would be ultimately packaged. Alternatively, the solutions can be freeze-dried in bulk, and the vials subsequently filled with amounts required to provide standardized solutions. The containers are then sealed, preferably retaining the contents under vacuum.

If the allergen is to be used on a solid support in a diagnostic procedure, the preformed support can be treated with the purified extract or with reconstituted allergen from the drying step previously described.

The diagnostic support preferably has a solid, water-insoluble surface. The surface can be widely varied. The surface may take different forms, have different physical characteristics, can be of different chemical compositions, and may be of one or more compositions as a mixture of compositions, coatings or laminates or combinations thereof. The surface may also be considered in accordance with its function. The surface serves as a base or substrate which will retain a discrete existance in the assay solution so as to be discernable from the medium and usually separable from the medium. The surface serves to support reagents bound to it so that they are incapable of diffusing through the solution independent of the surface. In addition, the surface acts as a support for the compounds conjugated with the materials bound to the surface, either as a base for a deposit layer or a support for covalent or non-covalent bonds. The surface is effectively non-fluid, discrete in that the surface is distinguishable from the liquid medium in which the surface is immersed, and provides a distinct base or foundation for supporting the compounds. The surface may exist in an electrostatically charged or uncharged form, being charged where such charges provide some advantage to the operation of a particular label system. The physical form of the support can embody any shape which is convenient for use including films, beads, containers, tubes, single and multiwelled plates and strips, and the like.

A wide variety of compounds can be employed as the solid support, the primary consideration being the binding of the reagents to the surface and the absence of interference with the reactions involved in the binding and use. A wide variety of organic and inorganic polymers, both natural and synthetic may be employed as the material for the solid support. Illustrative polymers include polyethylene, polypropylene, polybutylene, poly(4-methylbutylene), butyl rubber and other synthetic rubbers, silicone rubbers and silastic polymers, polyesters, polyamides, cellulose and cellulose derivatives (such as cellulose acetate, nitrose cellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be employed as the insoluble support may include silica gel, silicon wafers glass, paper, insoluble protein, metals, metalloids, metal oxides, magnetic materials, semi-conductive materials, cermets or the like. In addition are included substances that form gels, such as proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphiphilic compounds such as phospholipids, long chain (12–24 carbon atoms) alkyl ammonium salts and the like.

The surface will usually be polyfunctional or be capable of being polyfunctionalized so as to allow for covalent bonding between the reagents and the surface. Functional groups which may be present on the surface and used for linking can include carboxylic acids, aldehydes, amino groups, cyano groups, ethylenic groups, hydroxyl groups, or mercapto groups and the like. The manner of linking a wide variety of compounds to the various surfaces is well known and is amply illustrated in the literature, for example, "Immobilized Enzymes", Ichiro Chibata, Halsted Press, New York, 1978, and "Cuatrecasas", *J. Bio. Chem.* 245 3059(1970).

The lengths of the linking group may vary widely depending upon the nature of the compound being linked, the effect of the distance between the linked compound and the surface on the linked compound's properties, the potential for cross-linking of the linked compound, and the like. The linking group may be a bond or have up to about 12, usually not more than 10 atoms in a chain. The linking group may be aliphatic, alicyclic, aromatic, heterocyclic, or combinations thereof. The total number of atoms of the linking group will be not more than about 20, usually not more than about 16 atoms other than hydrogen, which will be carbon, oxygen as oxy or oxo, both oxo-carbonyl and non-oxo-carbonyl, nitrogen as amino or amido, or sulfur as thio or thiono. Illustrative groups include methylenecarbonyl, succinimidyl, alpha-haloacetyl, thiomethylene, glycyl or polyglycyl, succindioyl, malediooyl, glutardialkylidene, methylenephenyldiazo, and ureido.

A preferred diagnostic support of this invention comprises an opaque (preferably black) polystyrene or styrene-(vinyl monomer) copolymer having the allergenic extract bound thereto by absorption, adsorption, ionic bonding, van der Waals adsorption, electrostatic bonding, or other non-covalent bonding, or covalent bonding. A particularly advantageous support for this procedure comprises a microtiter plate or strip having a plurality of wells. The well surface or plastic cup inserts therein can constitute the allergenic extract support. Most advantageously, the microtiter plate or the well inserts are opaque to light so that excitation light applied to a well or fluorescense generated in response thereto does not reach or influence contents of the surrounding wells. With this system each well can be employed as a test system independent of the other wells.

For example, allergenic extracts of this invention can be applied by non-covalent bonding to a polystyrene microtiter well or polystyrene insert cup for a microtiter well by the following procedure. The polystyrene surface is washed with a cleaning liquid such as methanol. The extract, reconstituted in aqueous buffer solution is placed in the well or insert cup, incubated for 2 hours at room temperature, and removed. The well or insert cup is then rinsed with an aqueous sucrose or sorbitol solution and dried.

In one procedure for coating a polyethylene or polystyrene surface with allergenic extract, for example, the allergen is applied to the surface in a buffered solution containing an azide. A solution of allergenic extract having a concentration of from about 1 to about 100 micrograms of protein per ml is prepared from the allergenic extract in from about 0.005 to about 0.02 molar Tris-HCl (2-amino-2-hydroxymethyl-1,3-propanediol-HCl) and from about 0.01 to about 0.05 weight percent sodium azide. The Tris-HCl buffers the solution to a pH of from about 7.1 to about 9.5. This solution is then coated on the polymer surface and incubated at room temperature for from 6 to 72 hours and preferably from 12 to 48 hours. These coated surfaces are then washed with from about 0.005 to about 0.02 molar Tris-HCl having a pH of 6.9 to 8.4 and containing from about 0.01 to about 0.05 weight percent sodium azide. A 0.01 molar solution of Tris-HCl and 0.02 weight percent sodium azide buffered at a pH f 7.1 are preferred for both the incubation and the washing medium.

Additional details for preparing allergenic extracts for coating or the affixing of such to tubes or other apparatus is provided in the publication by C. M. Ling and L. R. Overby, "Prevalence of Hepatitis B. Antigen as Revealed by Direct Radioimmunoassay with $^{125}$I Antibody," *Journal of Immunology*, Vol. 109, No. 4, October 1972. Although the coating method has been described with reference to a coated tube, the coating method may be utilized to prepare coated inserts, beads, or any apparatus for use with wells, etc. by dipping the inserts in the allergenic extract solution and following the remaining procedure.

Preferably the allergen is covalently bonded to a water-soluble protein or protein-like polymer having an affinity for the insoluble substrate. The allergen-polymer product is then adhered to the insoluble substrate by non-covalent bonding such as by adsorption or absorption. This procedure is described in commonly assigned, copending application Ser. No. 444,622 filed Nov. 26, 1982, the entire contents of which are hereby incorporated by reference.

Suitable water-soluble proteins include bovine serum albumins of bovine (BSA), human (HSA), rabbit (RSA), goat (GSA), sheep (SSA), horse (HOSA), etc.; serum gamma globulin of the previously described animals; and other animal proteins such as ovalbumin, fibrinogen, thrombin, transferin, glycoproteins, etc. Suitable water-soluble amino acid polymers include polylysine, polyglutamic acid, polyalanine, polyhistidine, polymethionine, polyproline, etc. The allergen can be covalently bonded to water-soluble protein or amino acid polymer with conventional coupling agents using methods which are known in the art.

Preferably the coupling agent is a carbodiimide such as 1-ethyl-3-(3-N,N-dimethylaminopropyl)carbodiimide hydrochloride and 1-cyclohexyl-3(2-morpholinoethyl) carbodiimide methyl-p-toluenesulfonate. Other suitable coupling agents include aldehyde coupling agents having either ethylenic unsaturation such as acrolein, methacrolin, or 2-butenal or having a plurality of aldehyde groups such as glutaraldehyde, propanedial or butanedial. Other coupling agents include bifunctional NHS-esters such as disuccinimidyl suberate, disuccinimidyl tartarate, bis[2-(succinimidooxycarbonyloxy)ethyl]sulfone, disuccinimidyl (N,N'-diacetylhomocystine, dithiobis(succinimidyl propionate), ethylene glycolbis(succinimidyl succinate); heterobifunctional reagents such as N-5-azido-2-nitrobenzoyloxy succinimide, p-azidophenacyl bromide, p-azidophenylglyoxal, 4-fluoro-3-nitrophenyl azide, N-hydroxysuccinimidyl-4azidobenzoate, m-maleimidobenzoyl N-hydroxysuccinimide ester, methyl-4-azidobenzoimidate.HCl, p-nitrophenyl 2-diazo-3,3,3-trifluoropropionate, N-succinimidyl-6(4'-azido-2'-nitrophenylamino)hexanoate, succinimidyl 4-(N-maleimidomethyl)cyclohexane-1-carboxylate, succinimidyl 4-(p-maleimidophenyl)butyrate, N-succinimidyl (4-azidophenyldithio)propionate, N-succinimidyl 3-(2-pyridyldithio)propionate, N-(4-azidophenylthio)phthalimide, homobifunctional reagents such as 1,5-difluoro-2,4-dinitrobenzene, 4,4'-difluoro-3,3'-dinitrodiphenylsulone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate; and bifunctional imidoesters such as dimethyl adipimidate 2HCl, dimethyl suberimidate, dimethyl 3,3'-dithiobispropionimidate.2HCl, 2-iminothiolane.HCl. Covalent bonding of allergen to the insoluble protein can be carried out with the above reagents by conventional, well-known reactions, for example in the aqueous solutions at a neutral pH, at temperatures of less than 10° C. for 18 hours or overnight.

In an alternate procedure, the support surface can be first coated with an inert protein. This procedure is described with respect to polyethylene or polystyrene tubes but is equally suitable for wells, beads, etc. To the reactive bottom part, in accordance with this procedure, is attached an inert protein. The term "inert protein" means a protein which does not take part in the immunochemical reaction and does not adversely affect the biological substance. The proteins that can be used are well known to those skilled in the art. They include any proteinaceous material such as serum albumins or globulins obtained from various animal species or can be other uniform materials. Particularly preferred are bovine gamma globulin and gelatin since these are readily available. The proteinaceous material employed should be sufficiently homogeneous so that an essentially continuous surface can be obtained by the use thereof. Such a surface is readily obtainable with the above proteins. Allergenic extracts are then bonded to the inert proteins.

More specifically, the plastic surfaces are treated by a process which comprises (a) coating the surface by adsorption with an inert protein under adsorbing conditions, (b) attaching allergenic extract to the inert protein coating, (c) treating the coupled part with a stabilizing agent to stabilize the allergenic extract against denaturization, and (d) drying the reactive part under drying conditions that will not substantially denature the allergenic extract.

The amount of inert protein required to give optimum results is dependent on the nature of the inert protein, the surface and the allergenic extract. This amount is readily determinable by those skilled in the art. Typically, only a thin film (e.g., at least a thickness of one layer of molecules) of protein is attached to the surface. Generally, this is a sufficient amount to effect a uniform coating to which the biologically active substance may by attached.

The inert protein is readily attached to the surface to form a coating by spraying, soaking, or preferably by immersing the surface in an aqueous solution of inert protein such as an aqueous buffer solution under coating conditions. In this manner the protein is adsorbed to the surface. It is advantageous to use aqueous phosphate buffer solutions. Such buffers are described in U.S.P. XIX and are generally prepared using dipotassium hydrogen phosphate and potassium dihydrogen phosphate.

The inert protein is coated under adsorbing conditions which will not lead to denaturization of the protein. Specific pH and temperature conditions depend on the particular inert protein. Adsorbing conditions include conventional pH's, e.g. about 3 to 10 and conventional temperatures, e.g., about 20° C. to 30° C. While lower and higher application temperatures may be employed, for example as low as 4° C. and as high as 50° C., there is no significant advantage. In fact, at temperatures in excess of 50° C., the protein is generally denatured. At temperatures lower than 4° C. the protein is difficult to apply. For example, bovine gamma globulin is coated generally at a pH of 5 to 7 (optimally 6.4) at room temperature.

To facilitate attachment of the inert protein, the surface of the lower reactive part prior to attachment may be treated with solvents, surfactants, acids or bases. Surfactants, advantageously sodium dodecyl sulfate, are utilized as detergents to clean the surface and make it wettable. If the polymers contain carboxyl groups on the surface, it is often desirable to treat them with a saltforming base, e.g. KOH, to convert them to the salt form, thus giving them a negative charge which provides for enhanced electrical attraction and greater adsorption. The base also helps to clean the surface. In another aspect, it is advantageous to make the charge distribution on the surface about equal to that of the inert protein to be applied. This is accomplished by washing the surface with an aqueous buffer solution having about the same pH as the coating solution containing the inert protein prior to coating.

The allergenic extracts may be attached by any suitable means. Such suitable means known to the art include adsorption, covalent binding, ionic binding and entrapment. Methods for covalently binding the allergenic extracts to the inert protein are disclosed in U.S. Pat. Nos. 3,553,310 and 3,639,558, which are hereby incorporated by reference. A preferred method of covalent binding to inert protein comprises first treating the protein with an aldehyde coupling agent, followed by application of the allergenic extract under conditions which permit the aldehyde to covalently bind to both the inert protein and the allergenic extract. Suitable aldehyde coupling agents are those which have either ethylenic unsaturation or a plurality of aldehyde groups, or both, such as acrolein, methacrolein and 2-butenal. Dialdehydes can be employed such as glutaraldehyde, propanedial and butanedial.

When one of these aldehydes is contacted with the surface of the inert protein, the protein is stabilized and polymerized by cross-linking, and aldehyde active moieties are fixed to the surfaces. These moieties are believed to be carbonyl groups and are highly reactive to the amine groups of allergenic extracts since they form covalent bonds between the protein particles and the allergenic extracts.

The aldehyde or ethylenically unsaturated coupling procedures can also be used to covalently bond the allergens to other surfaces having primary amino groups. For example, polylysine coated polystyrene can be coupled to allergens with glutaraldehyde.

Alternative to aldehydes, there may be used other coupling moieties such as compounds having two or more of the following reactive groups: azo, sulfonic acid or fluoro groups activated by nitro groups, azide, imine or reactive chloro groups connected to a ring having appropriate resonance structure. These reactive groups are capable of reacting with the primary amino, sulfylhydryl, carboxylic, hydroxyl and phenolic groups in the substances constituting the inert protein as well as the allergenic extract substances to be coupled thereto.

A representative list of such coupling agents is bisdiazobenzadine, disulfonic acid, tetraazo-p-phenylenediamine difluorodinitrobenzene, difluorodinitrophenylsulfone, carbodiimides, toluene diisocyanate, cyanuric chloride, dichlorotriazine, N-t-butyl-5-methylisoxazolium perchlorate. Carbodiimides which can be employed are N,N-dicyclohexylcarbodiimide, 1-ethyl-3(3-dimethylaminopropyl)carbodiimide hydrochloride, and 1-cyclohexyl-3(2-morpholinyl(4)-ethylcarbodiimide)metho-p-toluene sulfonate.

Alternatively the allergenic extract can be attached by adsorption according to the procedure described in U.S. Pat. No. 3,551,555. The solid support surface can also be coated with a material which will bind to the allergens through an isocyanate bond such as that provided by polyether isocyanate coatings (HYPOL-2000, W. R. Grace & Co., Lexington, Mass.).

Procedures for binding reagents to glass surfaces are known in the art and are described in U.S. Pat. No. 4,280,992, for example. Methods used of binding the allergenic extract to the glass are not critical. Frosted glass is preferred. Allergenic extract may be bound to the glass surface by physical or chemical methods. The latter are preferred when firm and permanent binding of a large amount of allergenic extract to the glass is desired.

Binding by a physical method can be attained mainly by physical adsorption (van der Waals adsorption). Thus, the glass may be dipped in a solution of the allergenic extract and incubated, or allowed to stand, for an appropriate period of time to form physical binding. The solution can have a concentration of generally 0.01 to 400 g per liter and preferably 0.1 to 1.0 g per liter. The dipping or immersion treatment can be carried out, for example, at a temperature of 0° to 45° C. for one to 48 hours.

As a suitable chemical method, the allergenic extract can be bound to glass surfaces, and preferably frosted glass surfaces, with the aid of a silane coupling agent, and if necessary, a cross-linking agent. There may be used any silane coupling agent having in its molecule both a functional group reactive with the glass and a functional group reactive with the allergenic extract and/or the cross-linking agent. Examples of suitable functional groups reactive with the glass include those reactive with a silanol group of the glass, and include, for example, alkoxysilyl groups (such as methoxy or ethoxy-substituted silyl groups), and the like. Examples of suitable functional groups reactive with the allergenic extract and/or the cross-linking agent are those reactive with amino, carboxyl and/or thiol group(s), and include, for instance, carboxyl, epoxy, haloalkyl (such as chloroethyl and chloropropyl), aldehyde, primary and secondary amino, thiol, isocyanate, carboxylate, imino and nitrile (or cyano) groups, and the like. More specifically, examples of suitable functional groups reactive with the amino group are carboxyl, epoxy, haloalkyl and aldehyde groups. Suitable functional groups reactive with the carboxyl group include, for example, primary and secondary amino, and epoxy groups. Suitable functional groups reactive with the thiol group include thiol, epoxy, haloalkyl and aldehyde groups, and the like.

In binding the allergenic extract to the glass, the silane coupling agent may be used with or without the cross-linking agent. The crosslinking agent may be selected according to the kind of the silane coupling agent and the kind of the allergenic extract to be bound. There may be used any crosslinking agent which can crosslink the silane coupling agent with the allergenic extract. As such cross-linking agent there may be mentioned, those compounds that can cross-link the amino, carboxyl or thiol group of the silane coupling agent with the amino, carboxyl or thiol group of the immunologically active substance, such as those capable of producing a cross linkage between the thiol group and the thiol group, or between the amino group and the thiol group. Examples of suitable compounds which can crosslink between the amino group and the amino group are aliphatic dialdehydes (such as glyoxal, malonaldehyde, succinaldehyde, glutaraldehyde) and dichlorotriazines (such as 2-amino-4,6-dichloro-s-triazine), and the like. Suitable cross-linking agents between the thiol group and the thiol group are, for instance, dimaleimide compounds (such as N,N'-o-phenylenedimaleimide, N,N'-m-phenylenedimaleimide). Suitable cross-linking agents between the amino group and the thiol group are exemplified by maleimidocarboxyl-N-hydroxysuccinimide esters (such as m-maleimidobenzoyl-N-hydroxysuccinimide ester, and 4-(maleimidomethyl)cyclohexane-1-carboxyl-N-hydroxysuccinimide ester).

Adsorbents useful in the process of the invention as solid supports for allergenic extracts are known in the art. Suitable materials are listed below:

ADSORBENTS AND ABSORBENTS

Non-ionic cellulose
e.g., Whatman (Clifton, N.J., U.S.A.) types—
    CF-1 ®, long fiber powder
    CF-11 ®, medium fiber powder
    CC-31 ®, microgranular powder
    CC-41 ®, microgranular powder
e.g., Bio-Rad (Richmond, Calif., U.S.A.) types—
    Cellex ® N-1, powder
    Cellex ® 410, powder
Silica gel
e.g., Whatman type—SG 81, loaded paper; or Bio-Rad types—Bio-Sil ® A or Bio-Sil ® HA
Hydroxylapatite (Bio-Rad)
Alumina; acid, base, or neutral types (Bio-Rad)
Alumina C-gamma gel (Bio-Rad)
Calcium phosphate
Hydroxypropyl dextran
e.g., Pharmacia (Piscataway, N.J., U.S.A.) type—Sephadex ® LH 20
Dextran (Pharmacia)
Dextran sulfate (Pharmacia)
Alkyl agaroses
e.g., Pharmacia types—octyl-Sepharose ® Cl-4B or phenyl-Sepharose ® Cl-4B
e.g., Miles Research Products (Elkhart, Ind., U.S.A.) types—ω-amino alkyl agaroses
Lectin-agarose (Miles Research products)
Poly-L-lysine agarose (Miles Research Products)
Plastics, e.g., polystyrene, polyethylene, and polypropylene

ANION EXCHANGE MATERIALS

Diethylaminoethyl (CEAE) cellulose
e.g., Whatman types —
    DE-1 ®, floc
    DE-11 ®, powder
    DE-22 ®, fibrous
    DE-23 ®, fibrous
    DE-32 ®, dry, microgranular
    DE-52 ®, wet, microgranular
    DE-81 ®, paper
e.g., Bio-Rad type —Cellex ® D, fibrous
Diethylaminoethyl (DEAE) agarose
e.g., Bio-Rad type—DEAE Biogel ® A
Diethylaminoethyl (DEAE) dextran
e.g., Pharmacia type—DEAE Sephadex ®, bead
Aminohexyl-Sepharose ® 4B (Pharmacia)
Ecteola cellulose
e.g., Whatman types —
    ET-11 ®, powder
    ET-41 ®, powder (high purity)
    ET-81 ®, paper
e.g., Bio-Rad type—Cellex ® E, fibrous
Triethylaminoethyl (TEAE) cellulose
e.g., Bio-Rad type—Cellex ® T, fibrous
Diethyl-(2-hydroxypropyl)-amino (QAE) cellulose
e.g., Bio-Rad type—Cellex ® QAE, fibrous
Diethyl-(2-hydroxypropyl)-amino (QAE) dextran
e.g., Pharmacia type—QAE-Sephadx ®
Benzolyated diethylaminoethyl cellulose
e.g., Bio-Rad type—Cellex ® BD, fibrous

CATION EXCHANGE MATERIALS

Cellulose phosphate
e.g., Whatman types—
    P-1 ®, floc
    P-11 ®, powder
    P-41 ®, powder (high purity)
    P-81 ®, paper
Carboxymethyl cellulose
e.g., Whatman types—
    CM-1 ®, floc
    CM-11 ®, powder
    CM-22 ®, fibrous
    CM-23 ®, fibrous
    CM-32 ®, dry, microgranular
    CM-52 ®, wet, microgranular
    CM82 ®, paper
e.g., Bio-Rad type—Cellex ® CM, fibrous
Carboxymethyl dextran e.g., Pharmacia type—CM-Sephadex ®
Phosphoryl cellulose
e.g., Bio-Rad type—Cellex ® P, fibrous
Carboxymethyl agarose
e.g., Bio-Rad type—CM Biogel ® A
e.g., Pharmacia type—CH-Sepharose ® 4B
Sulphopropyl dextran
e.g., Pharmacia type—SP-Sephadex ®

Reagents formed by chemically coupling or combining the allergenic extract to polymeric carrier particles of varying particle size are well-known, e.g., U.S. Pat. Nos. 3,882,225; 3,957,931; 3,825,525; 3,629,558; 3,565,987, 3,553,310; 3,407,076; 3,236,732; 3,096,250; 4,092,114; 4,140,662; 4,210,723; 4,226,747; 4,259,313; 3,088,875; 3,766,013; 3,619,371; 3,809,613; 3,853,987; 3,963,441; 3,551,555; and 3,649,346. Netherlands Pat. No. 7,201,308; and British Pat. No. 1,257,263.

When covalent bonding of the allergenic extract to the polymer bead is desired, it is preferred to use for the bead a monomer which, after bead formation, retains a group which can react with amino, amido, or sulfonamido groups on the allergenic extract to be bound to the bead, e.g. chlorobenzyl, chloroacetyl, chloroethylcarbonyl, chloroethylsulfonyl, acryloyl, or vinyl-sulfonyl group.

Also the surface groups can be bonded to allergenic extract through bifunctional-linking groups reacted with the reactive bead surface group and with the allergenic extract.

The beads are usually prepared by polymerizing one or more vinyl monomers by standard procedures. Suitable vinyl monomers which can be polymerized and/or copolymerized with each other in any proportions and/or with other monomers to yield the desired beads include monovinylidene carboxyclic monomers, e.g., styrene, $\alpha$-methylstyrene, ar-(t-butyl)styrene, ar-methylstyrene, ar,ar-dimethylstyrene, ar-chlorostyrene, ar-(t-amyl) styrene, ar-bromostyrene, ar-fluorostyrene, ar-cyanostyrene, ar-methoxystyrene, ar-ethylstyrene, ar-hydroxymethylstyrene, ar-ethoxystyrene, ar-chloro-ar-methylstyrene, ar,ar-dichlorostyrene, ar,ar-difluorostyrene, vinyl naphthalene, and other such emulsion polymerizable monomers having not more than 26 carbon atoms; esters of $\alpha,\beta$-ethylenically unsaturated carboxylic acids which polymerize to form non-film forming polymers, e.g., methyl methacrylate, chloroethyl methacrylate, n-butyl methacrylate, ethyl methacrylate, isobutyl methacrylate, isopropyl methacrylate, phenyl methacrylate, butyl chloroacrylate, cyclohexyl chloroacrylate, ethyl chloroacrylate, methyl chloroacrylate, isopropyl chloroacrylate and other such esters capable of being polymerized to form hard polymers; $\alpha,\beta$-ethylenically unsaturated esters of non-polymerizable carboxylic acids, e.g., vinyl benzoate, vinyl toluate ar-ethylbenzoate, allyl ar-ethylbenzoate, vinyl trimethylacetate, vinyl pivalate, vinyl trichloroacetate and other such monomers wherein the unsaturated moiety has from 2 to 14 carbon atoms and the acid moiety has from 2 to 12 carbon atoms; $\alpha,\beta$-ethylencially unsaturated nitriles, e.g., such as nitriles having not more than 12 carbon atoms; other polymerizable vinyl monomers such as vinyl chloride, vinyl bromide and the like.

Key to successful treatment of allergic conditions is the accurate identification of the offending allergen and the titration of the affected animal to determine the desensitization dosage. In general, the reconstituted allergen extract is injected in sufficient quantity to cause major production of antigen-specific IgG and major production and/or activation of suppressor T lymphocytes. However, the quantity should not be sufficient to cause major allergic reaction and excessive antigen-specific IgE production. To the extent that antigen-specific IgE is produced at an increased level, it is critical that the IgG and suppressor IgE production is in such balance as to prevent allergic reaction.

The concentration and amount of the desensitization dosage are dependent upon many factors which are specific to the subject undergoing the allergic reaction. It is, therefore, necessary to titrate the patient to determine the proper dosage. A variety of standard techniques are available to carry out this procedure. Examples of traditional procedures are described in *Remington's Pharmaceutical Sciences*, supra, pp 1344–1352, the entire contents of which are incorporated herein by reference. The cutaneous or scratch test is performed by scarifying or making small abrasions on the skin of the patient and applying a small amount of the concentrated antigen. A positive reaction is indicated by a hive-like swelling and redness at the point of application, and is known clinically as a "wheal and flare" reaction. The reaction occurs in allergic individuals usually within 15 to 20 minutes. The size and appearance of the reaction provides a measure of the degree of sensitivity. Intracutaneous or intradermal testing is accomplished by injecting the allergenic material between layers of skin and observing the reaction. This test is more sensitive than the scratch test. Patch testing is a diagnostic procedure in which a small square of gauze or blotting paper, impregnated with allergen, is applied directly to the skin in order to elicit symptoms of allergic contact dermatitis. A reading is taken after 48 hours. By simultaneously applying a variety of allergens to selected skin areas, those causing allergic response can be identified, and the focus can be narrowed to those allergens involved in an allergic reaction. The targeted allergens can be applied in a serial fashion, that is, can be applied in graduated and increased doses so as to identify the concentration-sensitivity relationship.

For an in vitro method, allergen attached to a solid support such as spherical beads, paper discs or the surface of a well in a microtiter plate as described above can be used. When the patient's serum is mixed with the allergen-labeled disc or beads, IgE with specific affinity for the allergen binds to the allergen on the paper or bead surface. All non-specific IgE is removed by washing the disc or beads. Labeled anti-IgE can then be added, and after the appropriate incubation and washings, the label level is measured. The label level is correlated to the amount, if any, of allergen-specific IgE existing in the patient serum and, thereby, the degree of allergen sensitivity. To apply these systems, it is necessary to have special anti-IgE and allergen marked support materials and to label the anti-IgE used in the second incubation step. A most efficient in vitro method is described in commonly assigned copending application Ser. No. 462,585, filed Jan. 31, 1983, entitled FLUOROMETRIC ASSAY OF ALLERGIC REACTIONS AND REAGENTS THEREFOR by inventors Emanuel Calenoff, Ruth M. Jones, Yuh-geng Tsay and John R. Scott.

In view of the wide ranges in patient sensitivity and degree of allergic reaction, a dosage range for desensitizing treatment cannot be precisely predicted without testing. In general, the antigenic compositions of this invention are applied by standard procedures. They can be applied by injection intradermally, subcutaneously, intramuscularly, or administered orally, by inhalation, rectally or by other accepted means. The antigen composition is administered in a quantity of from 0.1 to 10,000 micrograms of antigen.

After identification of the offending allergen, hyposensitization immunotherapy procedures of this invention are employed. Exact mechanisms of this process are not fully understood. The procedure involves injecting into the host gradually increased doses of the composition of this invention, usually to maximum tolerated doses (doses not giving rise to major allergic response), at varying intervals in an attempt to develop IgG antibody protection against the agents and to increase the specific suppressor T lymphocyte activity. Booster injections to maintain the requisite IgG and suppressor T lymphocyte levels are required at intervals of one to four weeks. Usually the doses required for booster injections are substantially greater than the maximum dose required for control of the initial allergic reaction.

The injectable composition of this invention is an aqueous composition which contains one or more allergens which are substantially free from impurities, in combination with one or more physically acceptable, non-toxic excipients. For the injectable formulations, the concentration of allergen material is not critical and is determined by the dose needed per injection. In general, allergen concentrations of from 10 to 100,000 micrograms per ml can be used in the injectable composition.

The composition of this invention is used as an aqueous formulation. Certain aqueous vehicles are recognized officially because of their valued use in parenteral formulations. Often they are used as isotonic vehicles to which the antigen concentrate can be added at the time of administration. The additional osmotic effect of the allergen should not be enough to produce any discomfort when administered. These vehicles include Sodium Chloride Injection, Ringer's Injection, Coca's Solution, Evan's Solution, Dextrose Injection, Dextrose and Sodium Chloride Injection and Lactated Ringer's Injection.

The injectable compositions must be free from microbial and particulate contamination, free from pyrogen contamination, and to the extent they contain suspended solids, should be easily dispersed to form an injection mixture having a uniform concentration.

The excipients added can be those generally used for parenteral compositions. In general, these fall in the categories of isotonic salts, anti-microbial agents, buffers and antioxidants.

Any water-soluble, non-toxic salts generally used in adjusting the tonicity of parenteral solutions can be used. Sodium chloride is most commonly used. Other suitable salts are listed in *Remington's Pharmaceutical Sciences,* supra, pp 1405–1412 together with their isoosmotic concentrations, the content of which are hereby incorporated by reference.

Antimicrobial agents in bacteriostatic or fungistatic concentrations can be added, particularly to preparations contained in multi-dose containers. They must be present in adequate concentration at the time of use to prevent the multiplication of microorganisms inadvertently introduced into the preparation while withdrawing a portion of the contents with a hypodermic needle and syringe. The compounds generally approved and the concentration limit prescribed for each are set forth in the *United States Pharmacopeia* (USP). Suitable antimicrobial agents include phenylmercuric nitrate, thimerosal (0.01 weight percent), benzethonium chloride and benzalkonium chloride (0.01 weight percent), phenol or cresol, (0.5 weight percent), and chlorobutanol (0.5 weight percent). These concentrations are stated as those in the parenteral composition. Phenylmercuric nitrate is frequently employed in a concentration of 0.002 weight percent. Methyl p-hydroxybenzoate (0.18 weight percent), and propyl p-hydroxybenzoate (0.02 weight percent), in combination, and benzyl alcohol (2 weight percent) are also suitable.

The buffers are used primarily to stabilize a solution against the chemical degradation that would occur if the pH changed appreciably. Buffer systems employed should normally have as low a buffer capacity as feasible in order not to disturb significantly the body's buffer systems when injected. In addition, the buffer range and the effect of the buffer on the activity of the antigen is of concern. The acid salts most frequently used as buffers are water-soluble salts such as sodium, potassium, and ammonium citrates, acetates and phosphates.

Antioxidants can be used to preserve allergens which deteriorate during prolonged storage due to oxidation. Suitable antioxidants include sodium bisulfite (0.1 weight percent), acetone sodium bisulfite, sodium formaldehyde sulfoxylate, and thiourea. The sodium salt of ethylenediaminetetracetic acid chelates metal ions which would otherwise catalyze the oxidation reaction, and it will, therefore, sometimes enhance the activity of an antioxidant.

The anhydrous allergenic extract of this invention is stable, free from water (less than one percent water) and impurities. It can be free of excipients or it can contain pharmaceutically acceptable, non-toxic excipients which, when reconstituted with water or with normal parenteral solutions yield a composition suitable for parenteral administration according to the method of this invention. The amounts of antimicrobial agents and antioxidants present, if any, should yield a final concentration in a parenteral solution which falls within the range of those concentrations for each agent approved by the USP. Since the activities of the antimicrobial compounds and antioxidants are specific to each selected compound, a general overall range cannot be stated, the range being specifically selected based upon each drug in light of the USP-approved concentrations.

In general, the stable allergen extract contains from 0.01 to 99.9 weight percent allergenic extract. It can also optionally contain from 0 to 2 and preferably from 0.1 to 0.5 weight percent antimicrobial composition, and from 0 to 5 and preferably from 0.1 to 2 weight percent antioxidant. If the dry concentrate is to be mixed with a buffered isotonic parenteral solution to form the final parenteral injectable composition, it is unnecessary to have buffers and isotonic salts present in the dry concentrate. However, if the dry concentrate is to be reconstituted with distilled water, then it can contain from 0.1 to 5 and preferably from 0.5 to 2 weight percent of a buffering compound such as monobasic potassium phosphate, dibasic sodium phosphate, sodium bicarbonate or the like, and a sufficient quantity of an isotonic salt such as sodium chloride to provide an isotonic solution.

The parenteral composition for injection can be prepared from a dry concentrate, as indicated above, by mixing the concentrate with standard parenteral solutions, or alternatively, it can be reconstituted with distilled water. Typical standard parenteral solutions include Buffered Saline, Coca's Solution, Glycerinated Coca's Solution, Isotonic Sodium Chloride Solution, Sodium Bicarbonate Solution, Glycerin Saline Solution, Alcohol Saline Solution, Dextrose Solution (5%), and Dextrose Saline Solution. These solutions and their preparation are described in most pharmaceutical handbooks such as *Remington's Pharmaceutical Sciences,* supra, pp 1345, 1461–1487, which are hereby incorporated by reference.

STORAGE STABILITY TEST

Vacuum sealed vials containing 100,000 Activity Units of allergen (FDA recommended standard) are prepared.

1. At day zero, 3 vials of allergen are reconstituted and tested in triplicate by the IgE FAST TM inhibition test described in U.S. Pat. No. 4,528,267, and by the transparency test wherein light transmission (or absorbance) is measured throughout the range of 400 to 700 nm using a DU-8 Spectrophotometer (Beckman Instrument Co.). At the same time 6 vials are placed in a 38° C. incubator, 6 vials at 22° C. (room temperature), 12 vials in a 33° C. incubator and 12 vials in a 28° C. incubator.

2. After 8 days, a vial from each of the 38° C., 33° C. and 28° C. incubators are reconstituted and tested in triplicate by the inhibition test and transparency test. Two vials from each of the 22° C., 28° C. and 33° C. incubators are reconstituted and returned to the 22° C., 28° C. and 33° C. incubators.

3. After 2 more days, a previously reconstituted vial from each of the 22° C., 28° C. and 33° C. incubators are tested in triplicate by the inhibition test and transparency test.

4. After 15 days total (7 for the reconstituted vials), a vial from each of the 38° C., 33° and 28° C. incubators are reconstituted and tested in triplicate by the inhibition test and transparency test. A vial from each of the 22° C., 28° C. and 33° C. incubators which have been previously reconstituted are also tested in triplicate by the inhibition test and transparency test.

The potency can also be tested in the RAST test which is described by T. Foucard et al, *Int. Arch. Allergy Appl. Immunol.,* 43, 360; G. J. Gleich et al, *J. Allergy Clin. Immunol.,* 53, 158; and L. Yman, *Dev. Biol. Standard.,* 29, 151, the entire contents of which are hereby incorporated by reference.

In the test the allergens are reconstituted with 5 ml Delveccio's PBS solution having the following composition without breaking the seal.

| Potassium Chloride | 0.20 g/l |
|---|---|
| Potassium dihydrogen phosphate | 0.20 g/l |
| Sodium Chloride | 8.00 g/l |
| Disodium phosphate (Na₂HPO₄.7H₂O) | 2.16 g/l |
| Distilled water | qs 1.00 l |

This invention is further illustrated by the following specific but non-limiting examples.

EXAMPLE 1

Short Ragweed Extract

Defatting: To a 5 l round bottom flask of a Soxhlet extractor is added 4000 ml of diethyl ether and boiling stones. A 313.16 g quantity of pollen from perennial Short Ragweed (*Ambrosia artemisiifolia*) in an extraction thimble is placed in the Soxhlet extractor. The water flow through the condenser is begun, and the ether is heated under reflux (without excessive boiling) until return liquid is clear. The pollen is spread evenly on a paper tray and air-dried until no detectable ether is present to yield 278.46 g of defatted pollen.

Extraction: To an extraction vessel is added 100 g of defatted Short Ragweed pollen and 1000 ml of water (U.S.P. grade WFI). The extraction is continued for 17.5 hr at 4° C., and the solids are removed by passing the mixture through a cellulose filter paper.

Filtration and Ultrafiltration: The filtrate is clarified by passing it through a 0.5 micron filter. It is then passed through a 100,000 dalton ultrafilter to yield 800 ml of filtrate.

The solution is then ultrafiltered with a 1000 dalton filter until the solution volume remaining is reduced to 400 ml. To the remaining solution is added 400 ml of phosphate buffered saline, pH 7.4, and the reconstituted solution is again ultrafiltered until the solution volume remaining is 400 ml. This dilution and 1000 dalton ultrafilter sequence is repeated two more times, yielding a final volume of 400 ml of solution.

A 50 ml portion of the solution obtained in the previous step is mixed with 25 ml of wet (swelled) dextran (SEPHADEX G-25, Pharmacia) and 6 g of activated charcoal. The mixture is shaken gently, allowed to stand for 15 minutes at room temperature, and filtered through a 0.2 micron sterile filter apparatus. The residue is rinsed with 25 ml of phosphate buffered saline (pH, 7.4). The product solution is colorless.

Lyophilization: The solution was then placed in vials, each vial containing the equivalent of 5 ml of 1:10 wt/vol equivalent extract, i.e. sufficient solution to yield 100,000 Allergy Units (FDA recommended standard). The vials were frozen to −30° C. for 2 hours, vacuum was applied, the lyophilizer shelf was gradually heated to 25° C., and the freeze-drying was continued until constant weight was achieved to yield vials containing 100,000 units of desiccated Short Ragweed pollen extract having a moisture content of less than one weight percent.

EXAMPLE 2

Pollen Extracts

Repeating the procedure of Example 1 but replacing the Short Ragweed pollen with the following pollens yields the corresponding, colorless allergenic extracts being substantially free of components with molecular weights outside the 1000 to 100,000 dalton range and having a moisture content of less than one percent.

| | |
|---|---|
| Bermuda Grass | *Cynodon dactylon* |
| Western Ragweed | *Ambrosia psilostachya* |
| Perenneal Rye Grass | *Loluim perrene* |
| Johnson Grass | *Sorghum haleplese* |
| Timothy Grass | *Phleum prateuse* |
| Corn | *Zea mays* |
| Mountain Ceder | *Juniperus sabinoides* |
| English Plautain | *Plantago lanceolata* |
| White Ash | *Fraximus americana* |
| White Oak | *Quercus alba* |
| Box Elder | *Aces negundo* |
| White Alder | *Alnus rhombifolia* |
| American Elm | *Ulnus americana* |
| Bahia Grass | *Paspalum notatum* |
| Sagebrush | *Artemesia tridentata* |
| Orchard Grass | *Dactylis glomerata* |
| Russian Thistle | *Salsola kali* (pestifer) |
| Meadow Fescue | *Festuca elatior* |
| Olive | *Olea europaea* |
| Black river Birch | *Betula nigra* |

| | |
|---|---|
| Lamb's Quarters | *Chenopodium album* |

EXAMPLE 3

Pollen Extracts

Repeating the procedure of Example 1 with the following tree pollens, grass pollens and weed pollens yields the corresponding colorless extracts:

Tree pollens—Acacia—*Acacia Longifolia;* Acacia, Bailey's—*Acacia baileyana;* Ailanthus (See Tree of Heaven)—Ailanthus—*altissima;* Alder, Mountain (Tag) (Slender)—*ainus tenuifolia/icnana;* Alder, Red (Oregon)—*Alnus rubra;* Alder, Sitka—*Alnus sinuata;* Almond—*Prunus amygdalus;* Apple—*Pyrus malus (Malus pumila)*; Apricot—*Prunus armeniaca;* Arbor Vitae, Oriental (Ornamental)—*Thuja orientalis;* Ash, Arizona (Velvet—*Fraxinus velutina;* Ash, Blake—*Fraxinus nigra;* Ash, Green (Red)—*Fraxinus pennsylvanica;* Ash, Oregon—*Fraxinus oregona* (latifolia); Aspen—*Polulus tremuloides;* Bayberry (Sweet Gale)— *Myrica gale;* Beech, American—*Fagus grandifolia;* Birch, Cherry—*Betula lenta;* Birch, Paper—*Betula papyrifera;* Birch Spring—*Betula fontinalis;* Birch, White (Weeping-)—*Betula pendula;* Birch, Yellow—*Betula lutea;* Blue Beech (Am. Hornbeam)—*Carpinus carolineana;* Bottle Brush—*Callistemon citrinus;* Butternut—*Juglans cinerea;* Carob Tree—*Ceratonia siliqua;* Cedar, Deodar—*Cedrus deodora;* Cedar, Giant—*Thuja plicata;* Cedar, Incense—*Linocedrus decurrens;* Cedar, Japanese—*Cryptomeria japonica;* Cedar, Port Orford (Lawson Cypress)—*Chamaecyparis lawsoniana;* Cedar, Red—*Juniperus virginiana;* Cedar, Rocky Mountain—*Juniperus scopulorum;* Cedar, Salt (Tamarisk-)—*Tamarix gallica;* Cedar, White—*Thuja occidentalis;* Cherry, *Prunus cerasus;* Chestnut, American—*Castanea dentata;* Chestnut, Horse—*Aesculus hippocastanum;* Cottonwood, Black (Poplar, Western Balsam)—*Populus trichocarpa;* Cottonwood, Common—*Populus deltoides;* Cottonwood, Fremont—*Polulus fremontii;* Cypress, Arizona—*Cupressus arizonica;* Cypress, Bald (White)—*Taxodium distichum;* Cypress, Italian—*Cupressus sempervirens;* Cypress, Monterey—*Cupressus macrocarpa;* Elderberry—*Sambucus glauca;* Elm, Cedar (Fall Blooming)—*Ulmus crassifolia;* Elm, Chinese—*Ulmus parvifolia;* Elm, Siberian—*Ulmus pumila;* Elm, Slippery—*Ulmus fulva* (rubra); Eucalyptus (Blue Gum)—*Eucalyptus globulus;* Fir, Douglas—*Pseudotsuga menziesii;* Fir, Red (Noble)—*Abies nobilis (procera);* Fir, White—*Abies concolor;* Gum Sweet—*Liquidambar styraciflua;* Hackberry—*Celtis occidentalis;* Hazelnut, American—*Corylus americana;* Hemlock, Eastern—*Tsuga canadensis;* Hemlock, Western—*Tsuga heterophylla;* Hickory, Shagbark—*Carya ovata;* Hickory, Shellbark—*Carya laciniosa;* Hickory, White—*Carya tomentosa;* Ironwood (Hop-Hornbeam)—*Ostrya virginiana;* Juniper, California—*Juniperus californica;* Juniper, Chinese—*Juniperus chinensis;* Juniper, Oneseed—*Juniperus monosperma;* Juniper, Pinchot—*Juniperus pinchotti;* Juniper, Utah—*Juniperus osteosperma (juniperus utahensis)*; Juniper, Western—*Juniperus occidentalis;* Lilac—*Syringa vulgaris;* Linden (Basswood)—*Tila americana,* Locust, Black—*Robina pseudoacacia;* Maple, Big-Leaf (Coast)—*Acer macrophyllum;* Maple, (Hard Sugar)—*Acer saccharum;* Maple, Red—*Acer rubrum;* Maple, Soft (Silver)—*Acer saccharinum;* Melaleuca (Punk Tree)—*Melaleuca leucadendron;* Mesquite—*Prospopis juliflora;* Mock Orange, Wild (Syringa)—*Philadelphus lewisii;* Mulberry, Paper—*Broussonetia papyifera;* Mulberry, Red—*Morus rubra;* Mulberry, White—*Morus alba;* Oak, Arizona (Gambel)—*Quercus gambelii;* Oak, Arizona Scrub (Canyon)—*Quercus chrysolepsis;* Oak, Black (Yellow-)—*Quercus velutina;* Oak, Black Jack—*Quercus marilandica;* Oak, Bur—*Quercus macrocarpa;* Oak, California Black—*Quercus kelloggii-californica;* Oak, California Scrub—*Quercus dumosa;* Oak, Coast Live—*Quercus agrifolia;* Oak, Engelmann—*Quercus engelmanii;* Oak, Garry (Western White)—*Quercus garryana;* Oak, Holly—*Quercus ilex;* Oak, Interior Live—*Quercus wislizenii;* Oak, Post—*Quercus stellata;* Oak, Red—*Quercus rubra;* Oak, Swamp (Pin)—*Quercus palustris;* Oak, Valley—*Quercus lobata;* Oak, Virginia Live—*Quercus virginiana;* Oak, Water—*Quercus nigra;* Orange—*Citrus sinensis;* Osage Orange—*Maclura pomifera;* Palm, Date—*Phoenix dactylifera;* Palm, Dwarf—*Chamaerops humulis;* Palm, Canary Island Date (Ornamental)—*Phoenix canariensis;* Palm, Queen—*Cocos plumosa;* Peach—*Prunus persica;* Pear—*Pyrus communis;* Pecan—*Carya pecan;* Pepper Tree, California—*Schinus molle;* Pepper Tree, Brazilian—*Schinus terebinthifolius;* Pine, Australian (Beefwood)—*Casuarina equisetifolia;* Pine, Austrian—*Pinus nigra;* Pine, Canary Island-—*Pinus canariensis;* Pine, Digger—*Pinus sabiniana;* Pine, Loblolly—*Pinus taeda;* Pine, Lodgepole—*Pinus contorta;* Pine, Monterey—*Pinus radiata;* Pine, Pinyon—*Pinus edulis;* Pine, Red (Norway)—*Pinus resinosa;* Pine, Shortleaf—*Pinus echinata;* Pine, Virgina Scrub—*Pinus virginiana;* Pine, Western Yellow (Ponderosa)—*Pinus pondersa;* Pine, White (Eastern)—*Pinus strobus;* Pine, White (Western)—*Pinus monticola;* Plum (Prune)—*Prunus domestica;* Poplar, Balsam—*Populus balsamifera;* Poplar, Lombardy—*Populus nigra-italica;* Western Balsam (See Cottonwood, Black) *Populus trichocarpa;* Poplar, White—*Populus alba;* Privet—Ligustrum spp.; Redwood—*Sequoia sempervirens;* Russian Olive—*Elaeagnus angustifolia;* Spruce, Red—*Picea rubens;* Spruce, Sitka—*Picea sitchensis;* Sycamore, American (Eastern)—*Platanus occidentalis;* Sycamore, Mapleleaf—*Platanus acerifolia;* Sycamore, Western—*Platanus racemosa;* Tamarack (Larch)—*Larix occidentalis;* Tamarisk (See Cedar, Salt)—*Tamarix gallica;* Tree of Heaven—*Ailanthus altissima;* Walnut, Arizona—*Juglans rupestris;* Walnut, Black—*Juglans nigra;* Walnut, Hind's California Black—*Juglans hindsii;* Walnut, So. California Black—*Juglans californica;* Walnut, English—*Juglans regia;* Willow, Arroyo—*Salix lasiolepis;* Willow, Black—*Salix nigra;* Willow, Pussy—*Salix discolor;* Willow, Red—*Salix laevigata;* Willow, Yellow—*Salix lasiandra*

Grass and Weed pollens—Barley, Cultivated—*Hordeum vulgare;* Bent Grass, Colonial—*Agrostis tenuis;* Bluegrass, Annual—*Poa annua;* Bluegrass, Canada—*Poa compressa;* Bluegrass, Kentucky (June)—*Poa pratensis;* Bluegrass, Sandberg—*Poa sandbergii;* Brome BronchoRipgut—*Bromus rigidus;* Brome, California—*Bromus carinatus;* Brome, Cheat—*Bromus secalinus;* Brome, Smooth—*Bromus inermis;* Brome, Soft Cheat—*Bromus mollis;* Bunch, Blue (Northwestern Bunch)—*Agropyron spicatum;* Canarygrass—*Phalaris canariensis;* Canarygrass, Reed—*Phalaris arundinacea;* Fescue, Red—*Festuca rubra;* Grama Grass, Blue (Side Oats)—*Bouteloua gracilis;* Koeler's Grass (Western Junegrass)—*Koeleria cristata;* Lovegrass, Hawaiian—

*Eragrostis variabilis;* Oats, Common Cultivated—*Avena sativa;* Oatgrass, Tall—*Avena elatior (Arrhenatherum elatius);* Quack Grass—*Agropyron repens;* Redtop—*Agrostis alba;* Rye, Cultivated—*Secale cereale;* Ryegrass, Alkali—*Elymus triticoides;* Ryegrass, Giant Wild—*Elymus cinereus;* Ryegrass, Italian—*Lolium multiflorum;* Ryegrass, Western—*Elymus glaucus;* Salt Grass—*Distichlis stricta;* Sorghum, Common Cultivated—*Sorghum vulgare;* Sudan Grass—*Sorghum vulgare* var. *sudanese;* Sweet Vernal grass—*Anthoxanthum odoratum;* Velvetgrass—*Holcus Ianatus;* Wheat, Cultivated—*Triticum aestivum;* Wheatgrass, Crested—*Agropyron cristatum;* Wheatgrass, Western—*Agropyron smithii;* Alfalfa—*Medicago sativa;* Aster—*Aseter sinensis;* Balsam Root—*Balsamorhiza sagittata;* Bassia—*Bassia hyssopifolia;* Beach Bur—*Franseria bipinnatifida;* Burro Brush (Greasebush)—*Hymenoclea salsola;* Careless Weed—*Amaranthus palmeri;* Castor Bean—*Ricinus communis;* Cattail, Broadleaf—*Typha latifolia;* Clover, Red—*Trifolium pratense;* Clover, Sweet, Yellow—*Melilotus officinalis;* Clover, White (Dutch)—*Trifolium repens* (album); Cocklebur, Common—*Xanthium strumarium;* Cocklebur, Spiny—*Xanthium spinosum;* Cosmos—*Cosmos bipinnatus;* Daffodil—*Narcissus pseudonarcissus;* Dahlia—*Dahlia pinnata x coccinea;* Daisy/Chrysanthemum (Oxeyed Daisy)—*Chrysanthemum leucanthemum;* Dandelion—*Taraxacum officinale;* Dock, Bitter—*Rumex obtusifolius;* Dock, Yellow (Curly)—*Rumex crispus;* Dog Fennel (Mayweed)—*Anthemix cotula;* Fireweed, Alaska—*Epilobiium angustifolium,* Gladiolus—*Gladiolus Xhortulanus;* Goldenrod—Solidago spp; Greasewood—*Sarcobatus vermiculatus;* Hemp—*Cannabis sativa;* Hops—*Humulus lupulus;* Hopsage—*Grayia spinosa;* Iodine Bush (Burro Weed)—*Allenrolfea occidentalis;* Kochia (Mex. Firebush)—*Kochia scoparia;* Lily, Easter—*Lilium longiflorum;* Marigold—*Tagetes patula;* Marshelder, Burweed (Giant Poverty)—*Iva Xanthifolia;* Marshelder, Narrowleaf (August)—*Iva angustifolia;* Marshelder, True (Rough)—*Iva ciliata;* Mexican Tea—*Chenopodium ambrosiodes;* Mustard, Black—*Brassica nigra;* Mustard, Common Yellow—*Brassica campestris;* Nettle—*Urtica dioica* (gracilis); Pickleweed—*Salicornia ambigua;* Pigweed, Rough Redroot—*Amaranthus retroflexus;* Pigweed, Siny—*Amaranthus spinosus;* Poppy, California—*Eschoscholzia californica;* Povertyweed, Small—*Iva axillaris;* Rabbit Brush—*Chrysothamnus nauseosus;* Rabbit Bush (Bur Ragweed)—*Franseria deltoides;* Ragweed, Canyon—*Franseria ambrosiodes;* Ragweed, Desert—*Franseria dumosa;* Ragweed, False—*Franseria acanthicarpa;* Ragweed, Giant—*Ambrosia trifida;* Ragweed, Short—*Ambrosia artemisiifolia (elatior);* Ragweed, Silver—*Dicoria canescens;* Ragweed, Slender—*Franseria tenuifolia;* Ragweed, Southern—*Ambrosia bidentata;* Rose—*Rosa multiflora;* Sagebrush, Coast—*Arthemisia californica;* Sagebrush, Green (Tarragon)—*Artemisia dracunculus;* Sagebrush, Mugwort—*Artemisia vulgaris heterophylla;* Sagebrush, Pature (Carpet)—*Artemisi frigida;* Sagebrush, Sand Dune—*Artemisia pycnocephala;* Sagebrush, White (Prairie)—*Artemisia Iudovician;* Saltbush, Annual—*Atriplex wrightii;* Scale, All—*Atriplex polycarpa;* Scale, Bract—*Atriplex serenana bracteosa;* Scale, Brewers—*Atriplex lentiformis breweri;* Scale, Lens—*Atriplex lentiformis;* Scale, Red—*Atriplex rosea;* Scale, Silver (Fogweed)—*Atriplex argentea expansa;* Scale, Spear—*Atriplex patula hastata;* Scale, Wing (Shad)—*Atriplex canescen;* Scotch Broom—*Cytisus scoparius;* Sea Blite, California—*Suaeda californica;* Sedge—*Carex barbara;* Sheep Fat—*Atriplex confertifolia;* Sheep Sorrel—*Rumex acetosella;* Snapdragon—*Antirrhinum majus;* Suaeda (See Sea Blite); Sugar Beet—*Beta vulgaris;* Sunflower—*Helianthus annuus;* Waterhemp, Western—*Acnida tamariscina;* Winter Fat—*Eurotia lanata;* Wormseed (Jerusalem Oak)—*Chenopodium botrys;* Wormwood, Absinthe—*Artemisia absinthium.*

EXAMPLE 4

Epidermals and Glandular Elements

Repeating the procedures of Example 1 but replacing the Short Ragweed with cat hair and dander and with dog hair yields the corresponding extracts.

EXAMPLE 5

Epidermals and Glandular Elements

Repeating the procedures of Example 1 with the following colorless epidermals and glandular elements yields the corresponding extracts: Camel Hair & Dander; Cattle Hair & Dander; Deer Hair & Dander; Feathers, Chicken; Feathers, Duck; Feathers, Goose; Feathers, Parakeet; Feathers, Pigeon; Feathers, Turkey; Fox Fur; Gerbil Hair & Epithelium; Glue, Fish; Goat Hair & Dander; Guinea Pig Hair & Dander; Hamster Hair & Epithelium; Hog Hair & Dander; Horse Hair & Dander; Human Hair; Mink Fur; Mohair; Monkey Hair & Epithelium; Mouse Hair & Epithelium; Poodle Hair & Dander; Pyrethrum; Rabbit Hair & Epithelium; Rat Hair & Epithelium; Seal Fur; Wool, Sheep.

EXAMPLE 6

*Alternaria Tenuis* Extract

Repeating the procedures of Example 1 but replacing the Short Ragweed with the mold *Alternaria tenuis* yields the corresponding colorless extract.

EXAMPLE 7

Mold and Smut Extracts

Repeating the procedures of Example 1 with the following molds and smuts yields the corresponding colorless extracts:

Molds—*Aspergillus clavatus; Aspergillus fumigatus; Aspergillus glaucus; Aspergillus nidulans; Aspergillus niger; Aspergillus restrictus; Aspergillus sydowi; Aspergillus terreus; Botrytis cinerea; Candida albicans; Cephalosporium acremonium; Cephalothecium (Trichothecium) reseum; Chaetomium globosum; Cryptococcus terreus; Cunninghamella elegans; Curvularia spicifera; Dematium nigrum; Epicoccum nigrum; Epidermophyton floccosum; Fomes rimosus; Fusarium vasinfectum; Geotrichum candidum; Helminthosporium maydis; Helminthosporium; Hormodendrum (Cladosporium); Monilia sitophila; Mucor racemosus;* Mycogone sp.; *Neurospora crassa; Nigrospora sphaerica;* Oidiodendrum sp.; *Paecilomyces varioti; Penicillium artramentosum; Penicillium biforme; Penicillium carminoviolaceum; Penicillium chrysogenum; Penicillium digitatum; Penicillium expansum; Penicillium glaucum; Penicillium intricatum; Penicillium luteum; Penicillium notatum; Penicillium roqueforti; Penicillium roseum; Phoma herbarum;* Pleospora sp.; Poria sp.; *Pullularia pullulans; Rhizopus nigricans; Rhodotorula glutinis; Saccharomyces cerevisiae* (See Yeast Mix); *Scopulariopsis brevicaulis;* Spondylocladium sp.; *Sporobolomyces salmonicolor; Stemphylium botryosum; Streptomyces gri-*

*seus; Trichoderma viride; Typhula idahoensis; Verticillium albo-atrum.*

Smuts—Smut, Barley; Smut, Bermuda; Smut, Corn; Smut, Johnson; Smut, Oat; Smut, Sorghum; Smut, Wheat.

EXAMPLE 8

House Dust Extract

Repeating the procedures of Example 1 but replacing the Short Ragweed with house dust yields the corresponding colorless extracts.

EXAMPLE 9

Dust and Miscellaneous Extracts

Repeating the procedures of Example 1 with the following dusts yields the corresponding colorless extracts: Acacia Gum; Alfalfa Hay; Algae, Chlorella spp.; Carragheen Gum; Coconut Fiber; Cotton Linters; Cottonseed; Dust, Barley; Dust, Corn; Dust, Grain Mill; Dust, Mattress; Dust, Oat; Dust, Pea; Dust, Rye; Dust, Soybean; Dust, upholstery; Dust, Wheat; Dust, Wood—Cedar/Juniper; Dust, Wood—Fir/Hemlock; Dust, Wood—Gum; Dust, Wood—Mahogany; Dust, Wood—Maple; Dust, Wood—Oak Mix; Dust, Wood—Pine Mix; Dust, Wood—Redwood; Dust, Wood—Spruce; Dust, Wood—Walnut; Fern Spores, sp.; Flax Fiber; Flaxseed; Hemp; Jute; Kapok; karaya Gum; Lycopodium; Orris Root; Paper Mix; Pyrethrum; Silk; Sisal; Tragacanth Gum; Timothy Hay; Tobacco, Pipe; Tobacco, Cigarette; Tobacco, Cigar; Tobacco, Leaf.

EXAMPLE 10

Food Extracts

Repeating the procedure of Example 1 but replacing the Short Ragweed with the following foods yields the corresponding colorless extracts: Allspice; Almond; Apple Mix; Apricot Food; Arrowroot; Artichoke; Asparagus; Avocado; Banana; Barley, Whole (Grain); Bay Leaf; Bean, Kidney; Bean, Lima; Bean, Navy; Bean, Pinto-Frijole; Bean, String/Wax; Beef; Beet; Black-Eyed Pea; Blueberry; Brazil Nut; Buckwheat; Carrot; Cashew Nut; Celery; Cheese, Cheddar (American); Cheese, Parmesan; Cheese, Roquefort; Cheese, Swiss; Cherry Mix; Chewing Gum Base; chicken; Chicory; Chili Pepper; Chocolate/Cocoa; Cinnamon; Clam; Cloves; Cola; Coconut; Codfish Mix; Coffee; Corn, Whole (Grain); Crab; Cranberry; Cucumber; Curry Powder; Date; Dill; Egg White; Egg, Whole; Egg, Yolk; Eggplant; Endive; Garlic; Gelatine; Ginger; Grape/Raisin Mix; Grapefruit; Haddock; Halibut; Hazelnut (Filbert); Herring; Honey; Hope Food; Horseradish; Lamb; Lemon; Lentil; Lettuce Mix; Lime; Liver, Beef (Calves); Lobster; Mackerel; Malt; Mangoes; Maple, Syrup/Sugar; Melon, (see Muskmelon Mix); Milk, Cow's (Whole); Milk, Cow's (Albumin); Milk, Cow's (Casein); Milk, Cow's (Whey); Milk, (Evaporated); Milk, Goat's; Mint Mix (Peppermint/Spearmint); Mushroom; Mustard; Nutmeg; Oat, Whole (Grain); Okra; Olive Mix; Onion; Orange, Mandarin/Tangerine; Orange, Sweet; Oregano; Oyster Mix; Papaya; Paprika; Parsley; Parsnip; Pea; Peach Food; Peanut; Pear Food; Pecan Food; Pepper, Black/White; Pepper, Bell (Green/Red); Perch, Lake; Pineapple; Plum/Prune Mix; Poppy Seed; Pork; Potato, Sweet/Yam; Potato, White; Pumpkin; Rabbit Meat; Radish; Raspberry; Snapper; Rhubarb; Rice, Whole (Grain); Rice, Wild; Rye, Whole (Grain); Safflower Seed; Sage; Salmon; Scallops; Sesame Seed; Shrimp; Sole; Soybean, Whole (Grain); Spinach; Squash, Mix; Strawberry; Sugar (Beet); Sugar (Cane); Sunflower Seeds; Tapioca; Tea; Thyme; Tomato; Trout; Tuna Mix; Turkey; Turnip; Vanilla; Walnut Food, Black; Walnut Food, English; Watermelon; Wheat, Whole (Grain) Whitefish; Yeast, Bakers; Yeast, Brewers; Yeast Mix (Bakers/Brewers, *Sacchoromyces cerevisiae*).

EXAMPLE 11

Insect Extracts

Repeating the procedure of Example 1 but replacing the Short Ragweed pollen with the following insects yields the corresponding colorless extracts: Ant, (Black and Red); Ants, Carpenter; Ants, Fire; Aphid; Bee, Bumble; Bee, Honey; Blackfly; Butterfly; Caddis Fly; Cricket; Cockroach Mix; Deer Fly; Flea Antigen; Fruit Flies; Gnat sp.; Hornet, Black & Yellow; Horse Fly; House Fly; Mayfly sp.; Mite (*D. farinae*); Mosquito Mix; Moth, Miller; Wasp; Yellow Jacket.

EXAMPLE 12

Insect Venom Extracts

Repeating the procedures set forth in Example 1 but replacing the Short Ragweed pollen with the following insect venoms yields the corresponding colorless extracts: Honey Bee Venom—*Apis mellifera;* Wasp Venom Protein—*Polistes sp.;* White-Faced Hornet Venom Protein—*Dolichovespula maculata;* Yellow Hornet Venom Protein—*Dolichovespula arenaria;* Yellow Jacket Venom Protein—*Vespula sp.;* Mixed Vespid Venom Protein.

EXAMPLE 13

Microtiter plate prep., Perennial Ryegrass Extract

Black polystyrene microtiter plates are cleaned with methanol and dried. Perennial ryegrass pollen extract prepared in Example 2 is reconstituted in phosphate buffered saline, pH 7.5 and diluted 1:200 with the phosphate buffered saline solution.

A 100 microliter quantity of the diluted extract is pipetted into a microtiter plate well, incubated for 2 hr at room temperature and removed, and the well is washed 3 times with a 5 to 10% aqueous solution of sucrose or sorbitol and dried to yield a microtiter plate well having Perennial Ryegrass pollen extract on its surface.

EXAMPLE 14

Microtiter plate preparation

Following the procedure of Example 13, black polystyrene microtiter plates are cleaned with methanol, and selected wells thereof are incubated with diluted, reconstituted extracts prepared in accordance with Examples 1-12 to yield microtiter plate wells having the corresponding extracts on the surface thereof.

EXAMPLE 15

Miorotiter plate, covalent bonding of allergenic extracts

Microtiter plate well inserts having a polylysine coating thereon are treated with solutions of reconstituted allergenic extracts prepared in accordance with Examples 1-12 and glutaraldehyde to yield microtiter plate well inserts having the corresponding extracts covalently bonded thereto.

EXAMPLE 16

Microtiter Plate Preparation

To a solution of Short Ragweed allergen extract (3 mg/ml) prepared in accordance with Example 1 is added 10 microliters of a 5 wt/% bovine serum albumin (BSA) solution. After addition, the solution is kept at 4° C., and 5 mg of 1-Ethyl-3-(3-N,N-Dimethylaminopropyl) carbodiimide (ECDI) is added. The mixture is gently stirred at 4° C. for 20 minutes. The additions of both BSA and ECDI are repeated three more times. The final mixture is allowed to stand at 4° C. overnight to yield a conjugate of timothy grass pollen allergen covalently bonded to BSA.

The Short Ragweed allergen BSA conjugate is diluted in phosphate buffer, pH 8.5. To a well of a black microtiter plate is added precisely 100 microliters of the diluted conjugate solution. The coating process is allowed to proceed at room temperature for 2 hours (or overnight). At the end of the coating process, the liquid in each well is removed by aspiration. The wells are washed three times (3×200 microliters) with a phosphate washing buffer containing sorbitol and TRITON X405. The wells thus coated can be used for assaying patient serum for Short Ragweed pollen allergen specific IgE antibodies.

EXAMPLE 17

Following the procedure of Example 16, microtiter plate wells coated with BSA conjugates of the allergen extracts obtained in accordance with Examples 2-12 are obtained.

EXAMPLE 18

Short Ragweed Pollen Extract-Frosted Glass Conjugates

The one hundred frosted glass tubes are immersed in 100 ml of 0.5% solution of γ-amino-propyltriethoxysilane in acetone. After incubation at room temperature for 10 hr, the tubes are removed and washed with methanol and then with water. The tubes having the amino-containing silane coupling agent bound thereto are immersed in 40 ml of normal saline solution. A solution of 50 mg of allergenic extract from Short Ragweed pollen obtained in accordance with Example 1 in 10 ml of physiological saline solution and a solution containing 0.2% N-ethyl-N'-dimethylaminopropylcarbodiimide in 10 ml of physiological saline solution are added thereto. After treatment under immersion at 37° C. for 2 hours, the tubes are washed in sequence with water, 1M propionic acid aqueous solution and water, until no protein was detected in the washings.

The bound protein content can be measured by the method described by S. Moore et al, in Methods in Enzymology 6.819(1963). 10 pieces of the protein-glass conjugate are immersed in a solution of 6N HCl; and the whole system is sealed under reduced pressure and heated at 110° for 30 hrs. The protein content is measured by ninhydrin coloration.

EXAMPLE 19

Allergenic Extract—Frosted Glass Conjugate

Repeating the procedure of Example 18 but replacing the Short Ragweed pollen extract with the extracts obtained in Examples 2-12 yields the corresponding, respective allergenic extract-glass conjugates.

EXAMPLE 20

Allergenic Extract-Frosted Glass Conjugates

Two hundred frosted glass beads are immersed in 100 ml of 0.5% solution of γ-aminopropyltriethoxysilane in toluene and boiled for 7 hrs. The beads are then filtered off and washed with methanol and then with water. To the 200 frosted glass beads to which the amino containing silane coupling agent has been bound, there is added 100 ml of 2% glutaraldehyde aqueous solution. After standing for 2 hours at 4°, the beads are washed with deionized water 4 to 6 times until they did not carry the odor of glutaraldehyde any more. The 200 frosted glass beads so treated are then immersed in 40 ml of normal saline solution. Thereto is added a solution of 50 mg Golden Rod pollen allergenic extract in 10 ml of physiological saline. After allowing the reaction to proceed at 30° for 2 hrs, the glass beads are thoroughly washed with water until no protein is detected in the washings.

Repeating the above procedure but replacing the Golden Rod pollen extract with extracts obtained according to Examples 1-12 yields the corresponding allergenic extract-glass conjugates.

The invention claimed is:

1. A substantially dried, purified allergenic extract substantially free from extracted components with molecular weights outside the range of 1000 to 100,000 daltons, having an allergen composition substantially the same as the original extract, and which upon aqueous reconstitution yields a transparent, colorless solution which has an increase in absorbance in the range of 400 to 700 nm of less than 0.01 O.D. after storage for 18 days at 22° C.

2. An insoluble support to which a purified allergenic extract of claim 1 is adhered.

3. An insoluble support to which a conjugate of the purified allergenic extract of claim 1 and a water-soluble protein is adhered.

4. The purified stabilized allergenic extract of claim 1 wherein the extract is obtained from a member selected from the group consisting of pollens, epidermals, glandular elements, molds, smuts, insects, insect venoms and foods.

5. The purified allergenic extract of claim 4 obtained from a pollen.

6. The purified allergenic extract of claim 4 obtained from an epidermal or glandular element of an animal.

7. The purified allergenic extract of claim 4 obtained from a mold.

8. The purified allergenic extract of claim 4 obtained from a smut.

9. The purified allergenic extract of claim 4 obtained from an insect.

10. The purified allergenic extract of claim 4 obtained from an insect venom.

11. The purified allergenic extract of claim 4 obtained from a food.

12. A process for increasing stability of an allergenic extract comprising
   (a) passing an aqueous solution of an allergenic extract through 100,000 and 1000 dalton ultrafilters and retaining substantially all of the fraction having a molecular weight of from 1000 to 100,000 to yield an allergenic extract;

(b) contacting the allergenic extract obtained in Step (a) with a quantity of a carbon absorbent and with a gel polymer absorbent which forms a cage structure in aqueous media which is sufficient to clarify the extract, to yield a retained fraction; and (c) substantially drying the retained fraction obtained in Step (b) to yield an allergenic product which upon aqueous reconstitution yields a transparent, colorless solution which has an increase in absorbance in the range of 400 to 700 nm of less than 0.01 O.D. after storage for 18 days at 22° C.

13. A purified allergenic extract consisting essentially of the product of claim 12.

14. The process of claim 12 wherein the carbon absorbent has an average particle size of less than 200 mesh.

15. A purified allergenic extract consisting essentially of the product of claim 14.

16. The process of claim 12 wherein the allergenic extract is a fat-free, aqueous extract of a member selected from the group consisting of pollens, epidermals, glandular element, molds, smuts, insects, insect venoms and foods.

17. A purified allergenic extract consisting essentially of the product of claim 16.

18. The process of claim 12 wherein the swelled polymer is selected from the group consisting of a polysaccharide, polyacrylamide, polyvinylpyrrolidone and mixtures thereof.

19. A purified allergenic extract consisting essentially of the product of claim 18.

20. The process of claim 18 wherein the swelled polymer is a polysaccharide derived from dextran or agarose.

21. A purified allergenic extract consisting essentially of the product of claim 20.

22. The process of claim 20 wherein the carbon absorbent is activated charcoal having a particle size of less than 200 mesh and the swelled polymer is derived from dextran.

23. A purified allergenic extract consisting essentially of the product of claim 22.

* * * * *